United States Patent
Hull et al.

(10) Patent No.: US 9,606,250 B2
(45) Date of Patent: Mar. 28, 2017

(54) LOUDNESS BASED METHOD AND SYSTEM FOR DETERMINING RELATIVE LOCATION OF AN ACOUSTIC EVENT ALONG A CHANNEL

(71) Applicant: HiFi Engineering Inc., Calgary (CA)

(72) Inventors: John Hull, Calgary (CA); Seyed Ehsan Jalilian, Calgary (CA); Philip Cheuk, Calgary (CA)

(73) Assignee: Hifi Engineering Inc., Calgary, Alberta (CA)

( * ) Notice: Subject to any disclaimer, the term of this patent is extended or adjusted under 35 U.S.C. 154(b) by 496 days.

(21) Appl. No.: 13/958,358

(22) Filed: Aug. 2, 2013

(65) Prior Publication Data

US 2014/0036627 A1    Feb. 6, 2014

Related U.S. Application Data

(60) Provisional application No. 61/678,728, filed on Aug. 2, 2012.

(51) Int. Cl.
   *G01N 29/07* (2006.01)
   *G01N 29/11* (2006.01)
   (Continued)

(52) U.S. Cl.
   CPC ............ *G01V 1/001* (2013.01); *E21B 47/101* (2013.01); *G01N 29/11* (2013.01); *G01N 29/14* (2013.01);
   (Continued)

(58) Field of Classification Search
   CPC ........ G01N 29/07; G01N 29/11; G01N 29/14; G01N 29/36; G01N 29/44; G01N 29/4409;
   (Continued)

(56) References Cited

U.S. PATENT DOCUMENTS 5,205,173 A * 4/1993 Allen .................... G01M 3/243
                                                       73/40.5 A
5,974,862 A * 11/1999 Lander .................. G01M 3/243
                                                       702/51

(Continued)

FOREIGN PATENT DOCUMENTS

WO    WO 2008/098380      8/2008
WO    WO 2011/091505      8/2011

*Primary Examiner* — Laura Martin
*Assistant Examiner* — Rose M Miller
(74) *Attorney, Agent, or Firm* — Klarquist Sparkman, LLP

(57) ABSTRACT

A method for determining relative location of an acoustic event along a channel such as a wellbore includes obtaining two acoustic signals at are obtained at two different and known depths in the wellbore, dividing the acoustic signals into windows, and determining the relative loudnesses of pairs of the windows. The power of the acoustic signals may be used as a proxy for the loudness of the acoustic event, and this determination can be made in the time or frequency domains. The relative depth of the acoustic event can then be determined relative to the two known depths from the relative loudnesses. The acoustic event may be, for example, casing vent flow, gas migration, a leak along a pipeline, or sounds observed in an observation well from a nearby well in which fracking is being performed.

28 Claims, 13 Drawing Sheets

(51) Int. Cl.
| | |
|---|---|
| *G01N 29/14* | (2006.01) |
| *G01V 1/00* | (2006.01) |
| *G01S 5/18* | (2006.01) |
| *G01N 29/36* | (2006.01) |
| *E21B 47/10* | (2012.01) |
| *G01V 1/28* | (2006.01) |
| *G01N 29/44* | (2006.01) |

(52) U.S. Cl.
CPC .......... *G01N 29/36* (2013.01); *G01N 29/4409* (2013.01); *G01N 29/4454* (2013.01); *G01S 5/18* (2013.01); *G01S 5/186* (2013.01); *G01V 1/288* (2013.01); *G01N 29/07* (2013.01); *G01N 29/44* (2013.01); *G01V 2210/123* (2013.01); *G01V 2210/65* (2013.01)

(58) Field of Classification Search
CPC .... G01N 29/4454; G01V 1/001; G01V 1/288; G01V 2210/123; G01V 2210/65; G01S 5/18; G01S 5/186; E21B 47/101
USPC ....................................... 73/587, 592, 40.5 A
See application file for complete search history.

(56) References Cited

U.S. PATENT DOCUMENTS

| | | | | |
|---|---|---|---|---|
| 6,567,006 | B1* | 5/2003 | Lander | G01M 3/243 340/605 |
| 6,628,567 | B1* | 9/2003 | Prosser | G01H 1/00 367/13 |
| 6,725,705 | B1* | 4/2004 | Huebler | G01M 3/243 702/51 |
| 2003/0167847 | A1* | 9/2003 | Brown | G01M 3/243 73/592 |
| 2011/0301882 | A1* | 12/2011 | Andersen | G01F 1/666 702/54 |
| 2015/0034306 | A1* | 2/2015 | Hull | E21B 47/04 166/250.01 |

* cited by examiner

LOUDNESS BASED METHOD AND SYSTEM FOR DETERMINING RELATIVE LOCATION OF AN ACOUSTIC EVENT ALONG A CHANNEL

CROSS REFERENCE TO RELATED APPLICATION

Pursuant to 35 U.S.C. §119(e), this application claims the benefit of provisional U.S. Patent Application No. 61/678,728, filed Aug. 2, 2012 and entitled "Method and System for Determining Relative Depth of an Acoustic Event within a Wellbore," the entirety of which is hereby incorporated by reference.

TECHNICAL FIELD

The present disclosure is directed at methods, systems, and techniques for determining relative location of an acoustic event along a channel. More particularly, the present disclosure is directed at methods, systems, and techniques that determine the relative location of the acoustic event using the relative loudnesses of two or more acoustic signals generated by measuring the acoustic event at different and known locations along the channel.

BACKGROUND

During oil and gas drilling, a wellbore is drilled into a formation and then one or more strings of tubing or casing are inserted into the wellbore. For example, surface casing may line an upper portion of the wellbore and protrude out the top of the wellbore; one or both of production tubing and casing may be inserted into the wellbore to facilitate production; and intermediate casing, which is located between the production and surface casings, may also be present in the wellbore.

Gas migration and casing vent flow are both typical problems encountered during oil and gas drilling. For example, gas migration and casing vent flow can refer to any one or more of the following phenomena:

fluid flowing from the formation into an outermost annular portion of the wellbore behind an outermost casing string in the wellbore;

fluid flowing from the outermost annular portion of the wellbore into the formation; and fluid flowing across any of the casing or tubing strings in the wellbore.

In gas migration and casing vent flow, the moving fluid may be liquid or gaseous, and may eventually leak out of the wellbore and into the atmosphere, which harms the environment. Accordingly, when evidence of gas migration or casing vent flow is found, the location at which the fluid is flowing into the wellbore, the formation, or across the casing or tubing string is identified and a repair is performed. Such a process can be time intensive, costly, and inefficient.

Accordingly, research and development continue into methods, systems, and techniques that can be used to more robustly and efficiently identify and repair occurrences of gas migration and casing vent flow.

SUMMARY

According to a first aspect, there is provided a method for determining relative location of an acoustic event along a channel. The method comprises obtaining two acoustic signals at two different and known locations along the channel, wherein at least one of the acoustic signals includes the acoustic event; dividing each of the acoustic signals into windows, each of which has a certain duration; determining relative loudnesses of pairs of the windows, wherein each of the pairs comprises one window from one of the acoustic signals and another window from the other of the acoustic signals that substantially overlap each other in time; and determining the relative location of the acoustic event relative to the two known locations from the relative loudnesses.

The channel may comprise a wellbore; the relative location may be relative depth; and the acoustic event may comprise fluid flowing from formation into the wellbore, fluid flowing from the wellbore into the formation, or fluid flowing across any casing or tubing located within the wellbore. Alternatively, the acoustic event may comprise a leak along a pipeline (in which case the channel is the pipeline) or sounds observed in an observation well from a nearby well in which fracking is being performed (in which case the channel is the observation well).

The acoustic event may be fluid flowing from formation into the wellbore, fluid flowing from the wellbore into the formation, or fluid flowing across any casing or tubing located within the wellbore.

Both of the acoustic signals may comprise the acoustic event.

Obtaining the two acoustic signals may involve simultaneously measuring the acoustic event at the two different and known depths.

The windows that comprise any one of the pairs of the windows may represent concurrent portions of the acoustic signals.

The windows that comprise any one of the pairs of the windows may be time staggered such that the acoustic event is represented in both the windows of the pair.

The windows into which any one of the acoustic signals is divided do not have to overlap with each other.

Determining the relative loudnesses of each of the pairs of the windows may comprise determining relative powers of each of the pairs of windows by performing a method including, for each of the windows of the pair, determining the RMS amplitude of the portion of the acoustic signal within the window; and determining a loudness ratio comprising the ratio of the square of the RMS amplitude of a first of the windows of the pair relative to the sum of the squares of the RMS amplitudes of both of the windows of the pair.

Determining the relative loudnesses of each of the pairs of the windows may comprise determining relative magnitudes of each of the pairs of windows according to a method comprising for each of the windows of the pair, determining the RMS amplitude of the portion of the acoustic signal within the window; and determining a loudness ratio comprising the ratio of the RMS amplitude of a first of the windows of the pair relative to the total RMS amplitudes of both of the windows of the pair.

Determining the relative depth of the acoustic event may comprise obtaining an indication of the relative depth of the acoustic event from the loudness ratio; and determining whether the acoustic event is above the shallower of the two known depths or below the deeper of the two known depths by comparing each of the loudness ratios of the pairs of the windows to a ratio threshold, wherein one of the pairs indicates the acoustic event is above the shallower of the two known depths when the loudness ratio indicates that the acoustic event is louder at the shallower of the two known depths than the deeper of the two known depths, and one of the pairs indicates the acoustic event is below the deeper of the two known depths when the loudness ratio indicates that the acoustic event is louder at the deeper of the two known depths than the shallower of the two known depths.

Determining whether the acoustic event is above the shallower of the two known depths or below the deeper of the two known depths may comprise determining how many of the pairs indicates that the acoustic event is above the shallower one of the two known depths or below the deeper one of the two known depths; and determining whether the acoustic event is above the shallower one of the two known depths or below the deeper one of the two known depths from how many of the pairs indicate that the acoustic event is above the shallower one of the two known depths or below the deeper one of the two known depths.

The acoustic event may be determined to be above the shallower one of the two known depths when at least half of the pairs indicate that the acoustic event is above the shallower one of the two known depths, and otherwise may be determined to be below the deeper of the two known depths.

It may also be determined that the acoustic event is above a deemed reference depth when the acoustic event is determined to be above the shallower one of the two known depths, and that the acoustic event is below the deemed reference depth when the acoustic event is determined to be below the shallower of the two known depths. The deemed reference depth is midway between the two known depths.

The method may also comprise determining a measured time difference of the acoustic event as recorded in the acoustic signals; comparing the measured time difference to a minimum time difference; only using the loudness ratio to determine the relative depth of the acoustic event if the measured time difference equals or exceeds the minimum time difference; obtaining new acoustic signals corresponding to new known depths if the measured time difference is less than the minimum time difference, wherein the measured time difference of the acoustic event as recorded in the new acoustic signals equals or exceeds the minimum time difference; and determining the relative depth of the acoustic event using the new acoustic signals.

Obtaining the acoustic signals may comprise measuring the acoustic event at the two different and known depths using a fiber optic sensor assembly comprising a fiber optic cable having two pressure sensing regions spaced from each other, and each of the pressure sensing regions may have top and bottom ends and the minimum time difference may be the time for sound to travel between the top end of the deeper one of the pressure sensing regions to the bottom end of the shallower one of the pressure sensing regions.

The method may also comprise determining a measured time difference of the acoustic event as recorded in the acoustic signals; comparing the time difference to a maximum time difference; only using the magnitude ratio to determine the relative depth of the acoustic event if the time difference is less than or equals the maximum time difference; obtaining new acoustic signals corresponding to new known depths if the measured time difference exceeds the minimum time difference, wherein the measured time difference of the acoustic event as recorded in the new acoustic signals is less than or equal to the maximum time difference; and determining the relative depth of the acoustic event using the new acoustic signals.

Obtaining the acoustic signals may comprise measuring the acoustic event at the two different and known depths using a fiber optic sensor assembly comprising a fiber optic cable having two pressure sensing regions spaced from each other, and each of the pressure sensing regions may have top and bottom ends and the maximum time difference may be the time for sound to travel between the bottom end of the deeper one of the pressure sensing regions to the top end of the shallower one of the pressure sensing regions.

The method may also comprise graphing, using at least two types of indicators, on a plot comprising depth whether the acoustic event is above the shallower of the two known depths or below the deeper of the two known depths at various depths over which the acoustic event is measured.

The indicators may comprise two different colors.

The plot may further comprise time plotted versus the depth, wherein the plot shows whether the acoustic event is above the shallower of the two known depths or below the deeper of the two known depths at various depths and times over which the acoustic event is measured.

The acoustic event may have a frequency of between about 10 kHz to 250 kHz, and more particularly between about 2 kHz and 20 kHz.

The two different and known depths may be less than about 5 m apart.

The method may also comprise obtaining a third acoustic signal at a third different and known depth in the wellbore, wherein the third acoustic signal includes the acoustic event; and determining the relative depth of the acoustic event relative to one or both of (i) one of the two different and known depths and the third different and known depth and (ii) the other of the two different and known depths and the third different and known depth.

The relative depth of the acoustic event may be determined relative to the two different and known depths when the acoustic event is less than about 2 kHz, and the relative depth of the acoustic event may be determined relative to the third different and known depth and one of the other different known depths when the acoustic event is greater than about 2 kHz.

According to another aspect, there is provided a system for determining relative location of an acoustic event along a channel. The system comprises a sensor assembly comprising a cable having two sensors spaced from each other, wherein the sensor assembly is configured to measure the acoustic event using the two sensors and to correspondingly output two analog acoustic signals; a spooling mechanism on which the cable is wound and that is configured to lower and raise the cable into and out of the channel; a data acquisition box communicatively coupled to the sensor assembly and configured to digitize the acoustic signals; and a processor communicatively coupled to (i) the data acquisition box to receive the acoustic signals that have been digitized and a computer readable medium having encoded thereon statements and instructions to cause the processor to perform any of the aspects of the method described above or combinations thereof.

The cable may comprise a fiber optic cable and the sensors may comprise two pressure sensing regions.

According to another aspect, there is provided a non-transitory computer readable medium having encoded thereon statements and instructions to cause a processor to perform any aspects of the method described above or combinations thereof.

This summary does not necessarily describe the entire scope of all aspects. Other aspects, features and advantages will be apparent to those of ordinary skill in the art upon review of the following description of specific embodiments.

BRIEF DESCRIPTION OF THE DRAWINGS

In the accompanying drawings, which illustrate one or more exemplary embodiments.

DETAILED DESCRIPTION

Figure 1A:
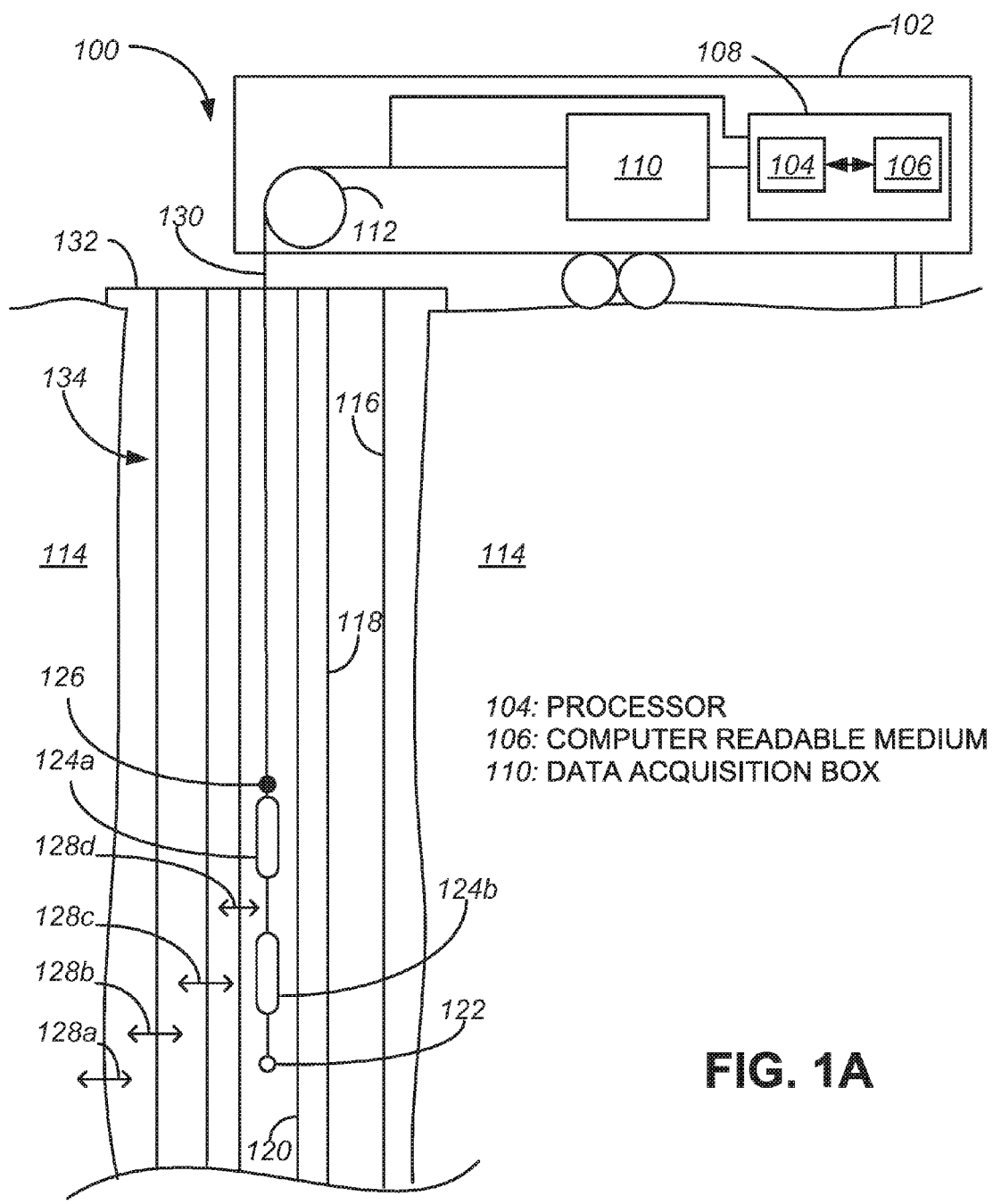
FIG. 1A shows a schematic of a system for determining relative location of an acoustic event along a channel in which the channel is a wellbore and location along the channel corresponds to depth, according to one embodiment.

Directional terms such as "top," "bottom," "upwards," "downwards," "vertically," and "laterally" are used in this description for the purpose of providing relative reference only, and are not intended to suggest any limitations on how any article is to be positioned during use, or to be mounted in an assembly or relative to an environment. Additionally, the term "couple" and variants of it such as "coupled," "couples," and "coupling" as used in this description are intended to include indirect and direct connections. For example, if a first device is coupled to a second device, that coupling may be through a direct connection or through an indirect connection via other devices and connections. Similarly, if the first device is communicatively coupled to the second device, communication may be through a direct connection or through an indirect connection via other devices and connections.

Casing vent flow ("CVF") and gas migration ("GM") are problems that are becoming increasingly significant in the oil and gas industry. CVF and GM may occur at any time during the life of a wellbore: while the wellbore is being drilled (pre-production); while the wellbore is being used to produce oil or gas; and while the wellbore is abandoned. The fluid migration that occurs within the wellbore during CVF and GM typically commences with fluid, such as a gaseous or liquid hydrocarbon, entering the wellbore from the formation into which the wellbore was drilled, entering the formation from the wellbore, or crossing any of the tubing or casing strings within the wellbore. When the fluid enters the wellbore from the formation or crosses the tubing or casing string (hereinafter collectively referred to as "leaks"), it makes a noise (hereinafter referred to as an "acoustic event"). This acoustic event can be detected using well logging.

The wellbore in which the CVF or GF occurs is one example of a channel along which acoustic events may occur and be monitored. Other examples of channels include a pipeline and an observation well drilled near to a well in which hydraulic fracturing ("fracking") is being performed. For the channel, acoustic events include events caused by leaks in the pipeline. For the observation well, acoustic events include sounds caused by creation or expansion of fractures in the fracking well.

The embodiments described herein are directed at a method and system for determining relative location of an acoustic event along a channel. One example used to describe this method and system is the example in which the channel is a wellbore, the acoustic event is caused by CVF or GM, and the method and system are used to determine the relative depth of the acoustic event in the wellbore. Once the source of the CVF or GM is located, repairs can be performed to end the CVF or GM. For example, if the CVF or GM is being caused by a crack in a tubing or casing string, this crack can be plugged. In the example in which the acoustic event is caused by CVF or GM, the depth of the acoustic event is determined relative to two different depths at which the acoustic event is measured from the difference in loudnesses of the acoustic event at those two different depths. The power of portions of the signals generated at those two different depths is used as a proxy for the loudness of the acoustic event. The signals generated at the two different depths are divided into windows, and the power of the portions of the signals within the windows are compared to each other to determine the relative depth of the acoustic event.

Referring now to FIG. 1A, there is shown a schematic of a system 100 for determining relative location of an acoustic event within a channel, according to one embodiment. In FIG. 1A, the channel comprises a wellbore 134 and location along the channel corresponds to depth of the wellbore 134. The wellbore 134 is drilled into a formation 114 that contains oil or gas deposits (not shown). Various casing and tubing strings are then strung within the wellbore 134 to prepare it for production. In FIG. 1A, surface casing 116 is the outermost string of casing and circumscribes the portion of the interior of the wellbore 134 shown in FIG. 1A. A string of production casing 118 with a smaller radius than the surface casing 116 is contained within the surface casing 116, and an annulus (unlabeled) is present between the production and surface casings 118,116. A string of production tubing 120 is contained within the production casing 118 and has a smaller radius than the production casing 118, resulting in another annulus (unlabeled) being present between the production tubing 120 and casing 118. The surface and production casings 116,118 and the production tubing 120 terminate at the top of the wellbore 134 in a wellhead 132 through which access to the interior of the production tubing 120 is possible.

Although the wellbore 134 in FIG. 1A shows only the production and surface casings 118,116 and the production tubing 120, in alternative embodiments (not shown) the wellbore 134 may be lined with more, fewer, or alternative types of tubing or casing. For example, in one such alternative embodiment a string of intermediate casing may be present in the annulus between the surface and production casings 116,118. In another such alternative embodiment in which the wellbore 134 is pre-production, only the surface casing 116, or only the surface and production casings 116,118, may be present.

FIG. 1A also shows four examples of leaks 128a-d (collectively, "leaks 128") that generate acoustic events. One of the leaks 128a corresponds to fluid crossing the formation 114's surface, either into the wellbore 134 from the formation 114 or vice-versa. Another of the leaks 128b corresponds to fluid crossing the surface casing 116, while a third leak 128c corresponds to fluid crossing the production casing 118, and a fourth leak 128d corresponds to fluid crossing the production tubing 120. As mentioned above, in alternative embodiments (not shown) the wellbore 134 may contain more, fewer, or other types of casing or tubing strings, and in such embodiments the leaks may result from fluid crossing any or more of these strings.

Lowered through the wellhead 132 and into the wellbore 134, through the production tubing 120, is a fiber optic sensor assembly. The fiber optic sensor assembly includes a fiber optic cable 130 that is optically coupled, via an optical connector 126, to a pair of pressure sensing regions 124: a shallower pressure sensing region 124a that is located at a shallower depth than a deeper pressure sensing region 124b; each of the pressure sensing regions 124a,b is hereinafter referred to as a "sensor" 124a,b, and the pressure sensing regions 124 collectively are referred to as the "sensors" 124. Each of the sensors 124 is located along its own fiber optic strand and is sensitive to strains that result from detection of the acoustic event. The fiber optic assembly also includes a weight 122 coupled below the lower sensor 124b to help ensure the fiber optic cable 130 is relatively taut during well logging. An exemplary fiber optic sensor assembly is described, for example, in PCT patent application having serial number PCT/CA2008/000314, publication number WO/2008/098380, and entitled "Method and Apparatus for Fluid Migration Profiling", the entirety of which is hereby incorporated by reference herein. In an alternative embodiment (not depicted), a single fiber strand that has multiple sensors on it may be used, with the signals from the multiple sensors being multiplexed back to the surface. In other alternative embodiments different types of sensor assemblies may be used. For example, non-fiber based assemblies, such as electrical assemblies and piezoelectric sensors, may be used.

The fiber optic strands themselves may be made from quartz glass (amorphous $SiO_2$). The fiber optic strands may be doped with a rare earth compound, such as germanium, praseodymium, or erbium oxides) to alter their refractive indices. Single mode and multimode optical strands of fiber are commercially available from, for example, Corning® Optical Fiber. Exemplary optical fibers include ClearCurve™ fibers (bend insensitive), SMF28 series single mode fibers such as SMF-28 ULL fibers or SMF-28e fibers, and InfiniCor® series multimode fibers.

Figure 2A:
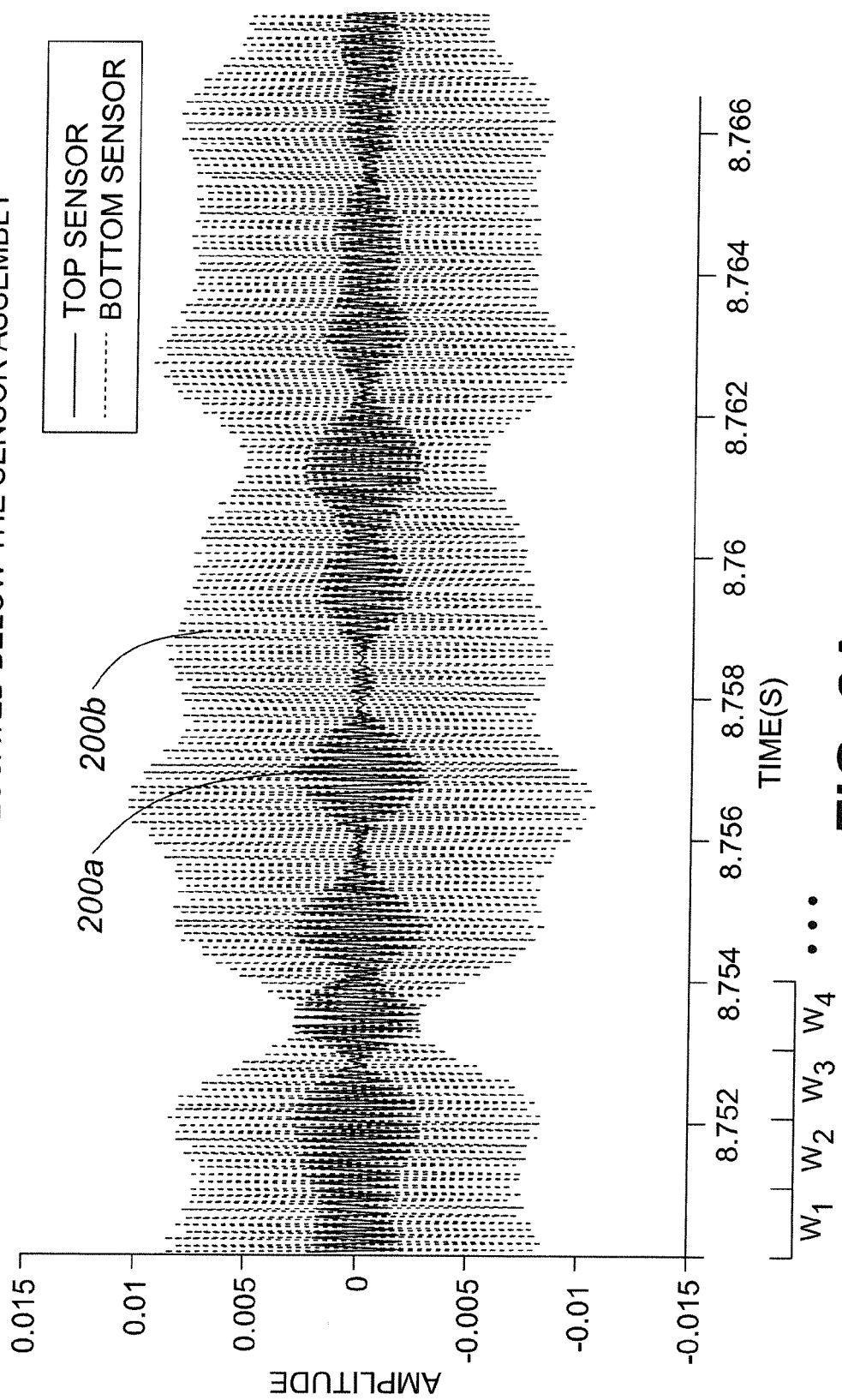
FIGS. 2A and 2B show waveforms of acoustic signals recorded using top and bottom sensors comprising part of the system of FIG. 1A and positioned at two different and known depths within the wellbore.
Figure 2B:
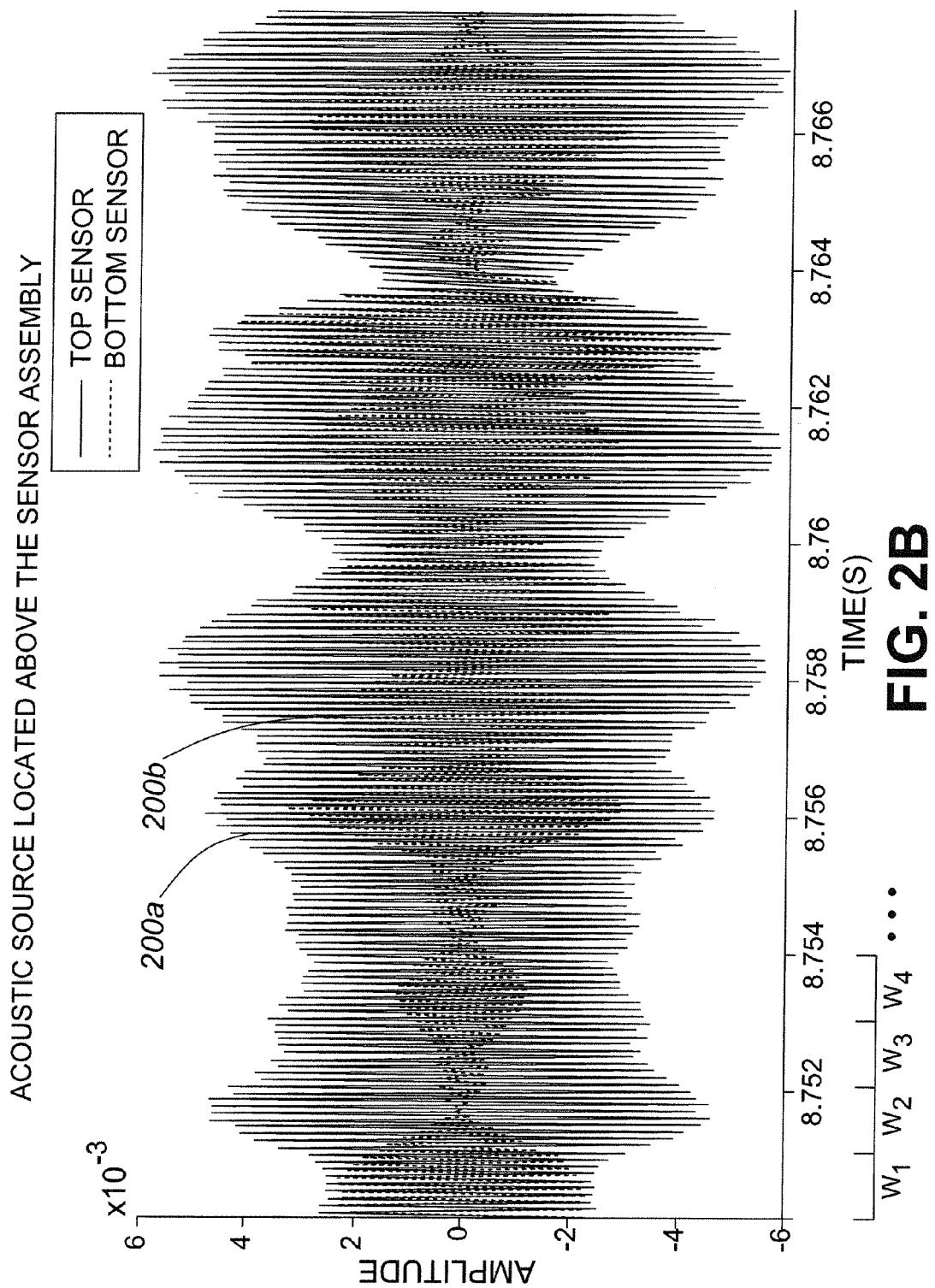
Figure 6:
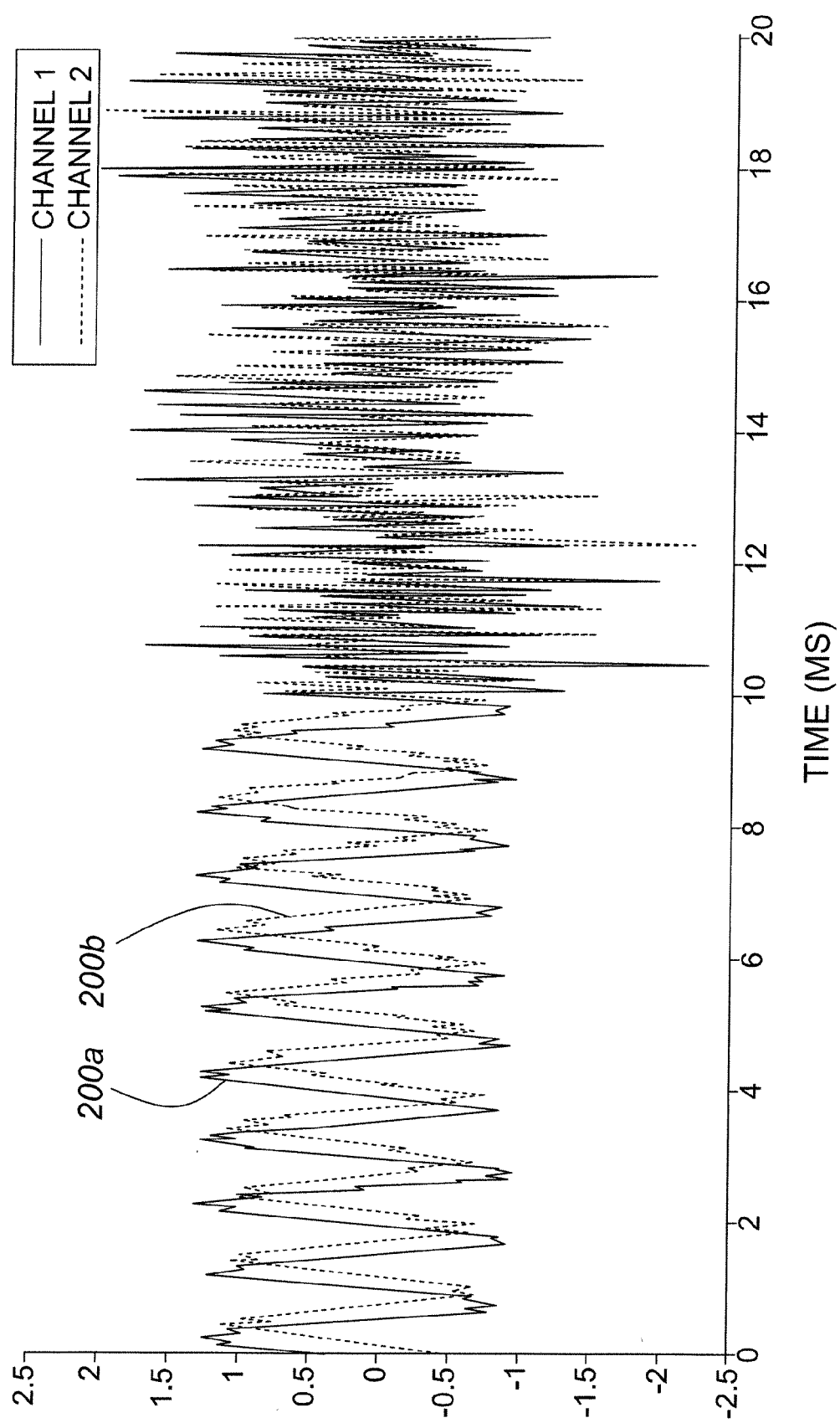
FIG. 6 depicts another pair of acoustic signals acquired using the system of FIG. 1A, in which a relatively high level of noise is present for approximately half the signals' duration.

When the sensors 124 detect the acoustic event, they generate acoustic signals 200a,b (collectively, "acoustic signals 200", which are not shown in FIG. 1A but are shown in FIGS. 2A and 2B and FIG. 6) that are transmitted to the surface. The shallower, or "top", sensor 124a generates one of the acoustic signals 200a and the deeper, or "bottom", sensor 124b generates the other of the acoustic signals 200b. The acoustic signals 200 generated by the sensors are transmitted along the fiber optic cable 130, past a spooling device 112 around which the fiber optic cable 130 is wrapped and that is used to lower and raise the cable 130 into and out of the wellbore 134, and to a data acquisition box 110. The data acquisition box 110 digitizes the acoustic signals 200 and sends them to a signal processing device 108 for further analysis. The digital acquisition box 110 may be, for example, an Optiphase™ TDI7000.

The signal processing device 108 is communicatively coupled to both the data acquisition box 110 to receive the digitized acoustic signals and to the spooling device 112 to be able to determine the depths at which the acoustic signals 200 were generated (i.e. the depths at which the sensors 124 were when they measured the acoustic event), which the spooling device 112 automatically records. The signal processing device 108 includes a processor 104 and a non-transitory computer readable medium 106 that are communicatively coupled to each other. The computer readable medium 106 includes statements and instructions to cause the processor 104 to perform any one or more of the exemplary methods depicted in FIGS. 4 and 5, below, which are used to determine the relative depth of the acoustic event. The spooling device 112, data acquisition box 110, and signal processing device 108 are all contained within a trailer 102 to facilitate transportation to and from the wellbore 134.

Figure 1B:
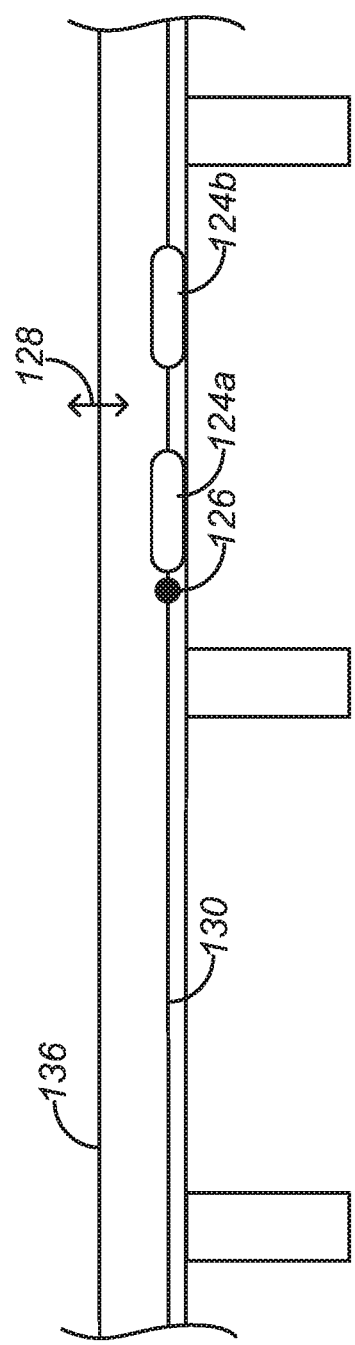
FIG. 1B shows a channel comprising a pipeline being used in conjunction with an example embodiment of the system of FIG. 1A.

Referring now to FIG. 1B, there is shown a portion of a pipeline 136 being used in conjunction with an exemplary embodiment of the system 100. In addition to the pipeline 136, FIG. 1B depicts an exemplary embodiment of the fiber optic sensor assembly comprising the cable 130, optical connector 126, and sensors 124. A leak 128 is shown in the pipeline 136.

Figure 4:
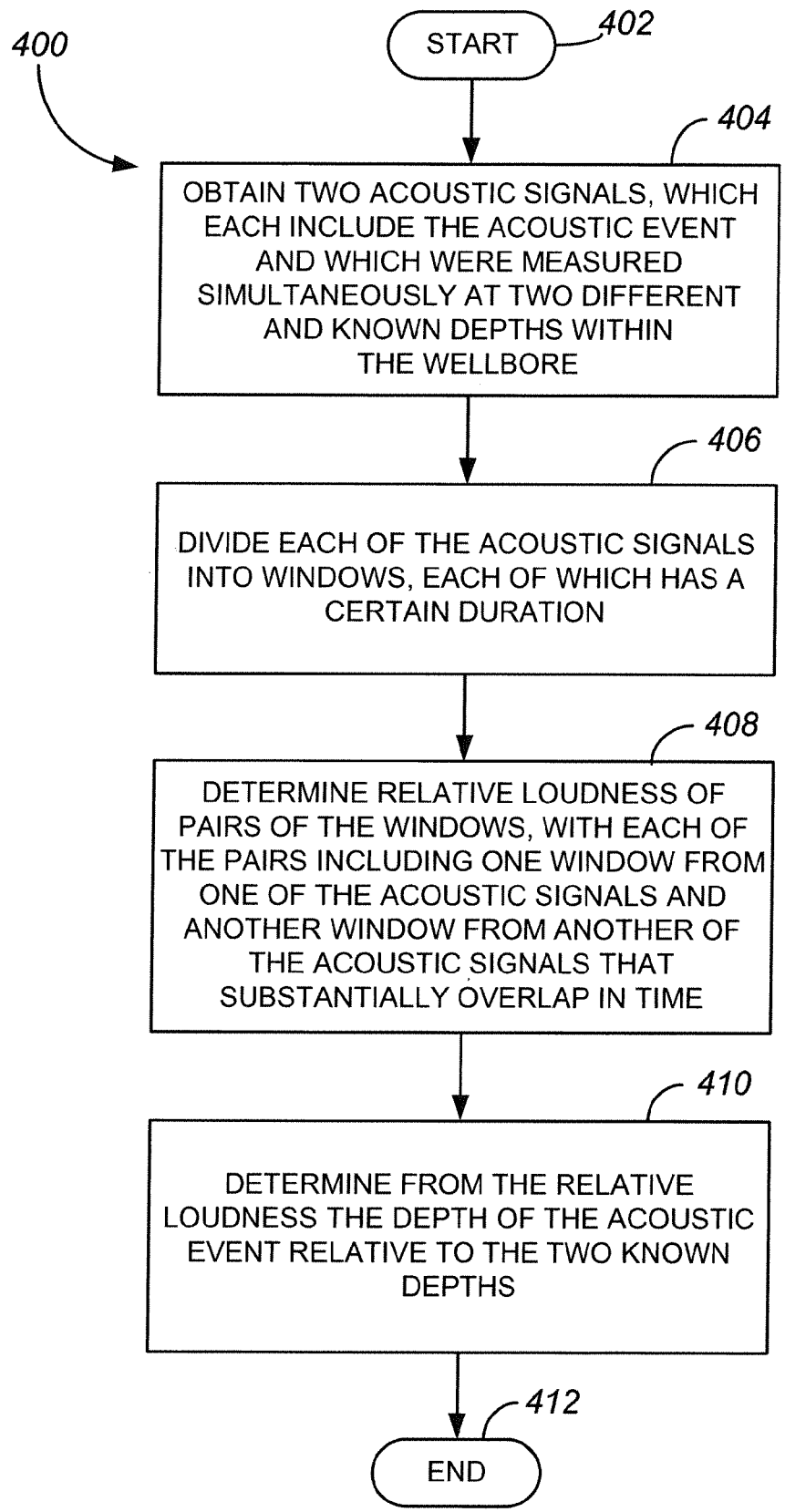
FIG. 4 shows a method for determining the relative depth of the acoustic event within the wellbore, according to another embodiment.

Referring now to FIG. 4, there is shown a method 400 for determining the relative depth of the acoustic event within the wellbore, according to another embodiment. The method 400 may be encoded on to the computer readable medium 106 to cause the processor 104 to perform the method 400 on the acoustic signals 200 that the signal processing device 108 receives from the data acquisition box 110. At block 402, the processor 104 begins performing the method 400. At block 404, the processor 104 acquires the acoustic signals 200 from the data acquisition box 110. As mentioned above, because each of the acoustic signals 200 is generated using one of the sensors 124, the depths of which are known from the spooling device 112, the processor 104 knows the depths at which each of the acoustic signals 200 was measured.

Although not shown in FIG. 4, the processor 104 filters the acoustic signals 200 prior to performing any further signal processing on them. In order to condition the signals 200 for further processing, in the depicted embodiment the processor 104 filters the acoustic signals 200 through a 10 Hz high pass filter, and then in parallel through a bandpass filter having a passband of between about 10 Hz to about 200 Hz, a bandpass filter having a passband of about 200 Hz to about 600 Hz, a bandpass filter having a passband of about 600 Hz to about 1 kHz, a bandpass filter having a passband of about 1 kHz to about 5 kHz, a bandpass filter having a passband of about 5 kHz to about 10 kHz, a bandpass filter having a passband of about 10 kHz to about 15 kHz, and a high pass filter having a cutoff frequency of about 15 kHz. The processor 104 can digitally implement the filters as, for example, $5^{th}$ or $6^{th}$ order Butterworth filters. By filtering the acoustic signals 200 in parallel in this manner, the processor 104 is able to isolate different types of the acoustic events that correspond to the passbands of the filters. In an alternative embodiment (not shown), the filtering performed on the acoustic signals 200 may be analog, or a mixture of analog and digital, in nature, and may be partially or entirely performed outside of the signal processing device 108, such as in the data acquisition box 110. Alternative types of filters, such as Chebychev or elliptic filters with more or fewer poles than those of the Butterworth filters discussed above may also be used, for example in response to available processing power.

Examples of two acoustic signals 200 corresponding to one of these passbands and generated simultaneously from measuring the same acoustic event at different depths are shown in FIGS. 2A and 2B. In FIGS. 2A and 2B the acoustic event emits a signal of 10 kHz. In this context, "simultaneously" refers to measuring the acoustic event from time=$t_0$ to time=$t'$ at both of the sensors 124, where time is measured at a reference point away from and stationary relative to the sensors 124. In FIGS. 2A and 2B, the acoustic signal 200a shown in a solid line is generated with the shallower sensor 124a, while the acoustic signal 200b shown in a dashed line is generated with the deeper sensor 124b. In FIG. 2A the acoustic event is generated below the deeper sensor 124b and are therefore nearer to the deeper sensor 124b than the shallower sensor 124a, and the acoustic signal 200b generated with the deeper sensor 124b accordingly has a larger average value than the signal 200a generated with the shallower sensor 124a. Conversely, in FIG. 2B, the acoustic event is generated above the shallower sensor 124a, and the acoustic signal 200a generated with the shallower sensor 124a accordingly has a larger average value than the signal 200b generated with the deeper sensor 124b.

At block 406 the processor 104 divides each of the acoustic signals 200 into windows $w_1 \ldots w_n$. To illustrate this, the signals 200 shown in FIGS. 2A and 2B are divided into windows, and the first four windows $w_1 \ldots w_4$ for each of the signals 200 are labeled. The outputs of each of the filters that filter the acoustic signals 200 in parallel are divided into windows; in the above example in which four different filters are used to filter the acoustic signals 200 in parallel, four different pairs of the acoustic signals 200 are windowed. For any given integer $k \in [1 \ldots n]$, $w_k$ for one of the acoustic signals 200 and $w_k$ for the other of the acoustic signals 200 together constitute a pair of the windows, or a "window pair", $w_{k\_pair}$. The duration chosen for each of the windows may range from 0.001 s to greater than 1 s. In FIGS. 2A and 2B, the windows are each 0.001 s long. In the depicted embodiment, because each of the windows in one of the acoustic signals 200 has a counterpart in the other acoustic signal 200 with identical start and end times, any given window pair $w_{k\_pair}$ for the acoustic signals 200 represents concurrent portions of the signals 200. In an alternative embodiment, the windows of any given window pair $w_{k\_pair}$ do not have to be concurrent, but may, for example, be non-concurrent but substantially overlap each other such that their relative powers nonetheless remain indicative of whether the acoustic event is nearer to the shallower sensor 124a or the deeper sensor 124b, as discussed in more detail below.

Figure 5:
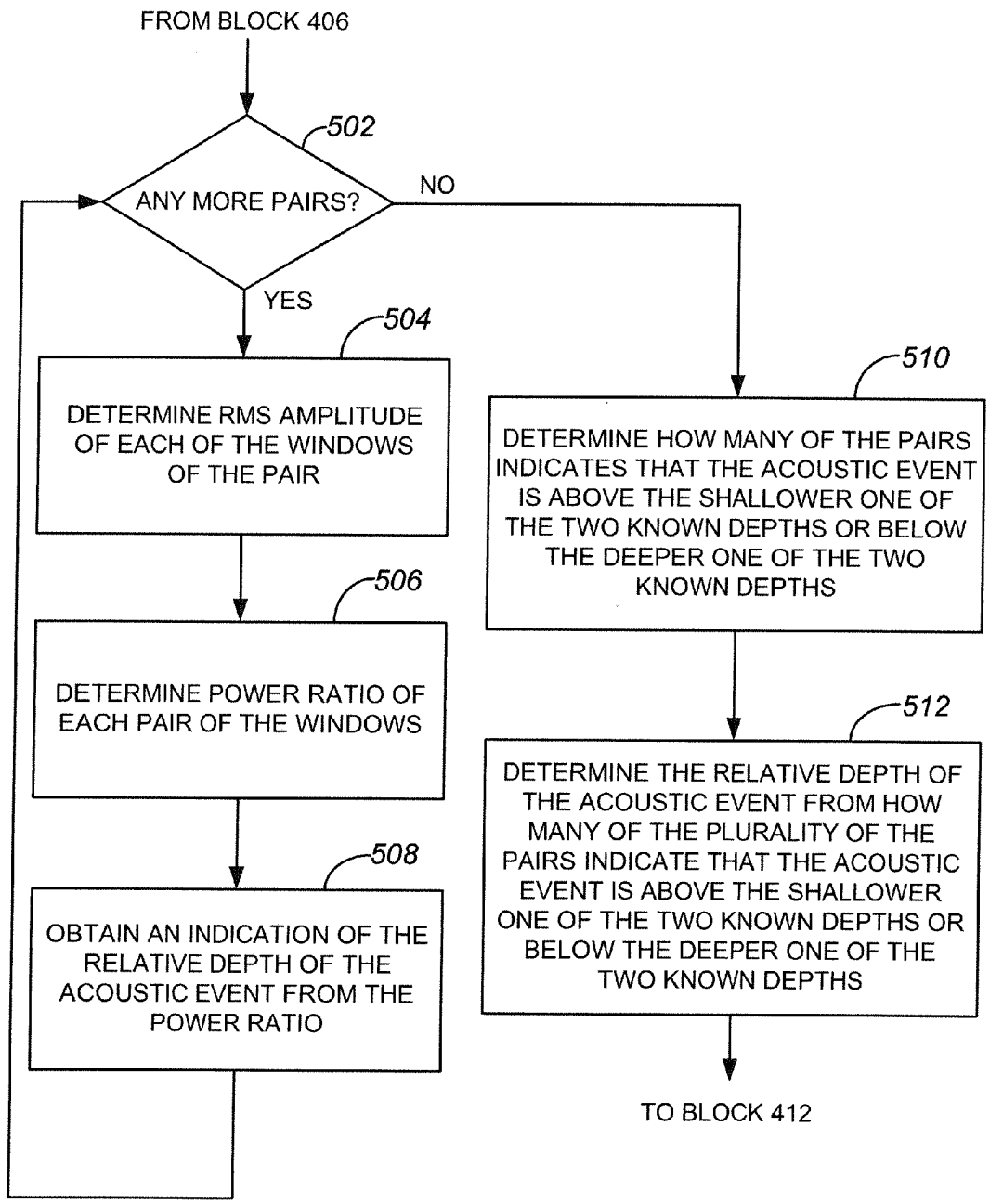
FIG. 5 shows an embodiment of a method for determining relative power of the acoustic signals and for determining the relative depth of the acoustic event from the relative power of the acoustic signals, which can comprise part of the method of FIG. 4.

After dividing the acoustic signals into the windows $w_1 \ldots w_n$, the processor 104 at block 408 determines the relative loudnesses of the portions of the acoustic signals 200 contained in each of the window pairs $w_{k\_pair}$ for $k \in [1 \ldots n]$, and from these relative loudnesses determines, at block 410, the depth of the acoustic event relative to the known depths of the sensors 124. Loudness of the acoustic signals 200 can be represented in several ways. Referring now to FIG. 5, there is shown one embodiment of a method by which the processor 104 may perform blocks 408 and 410 and in which the power of the acoustic signals 200 is used as a proxy for loudness.

Figure 2C:
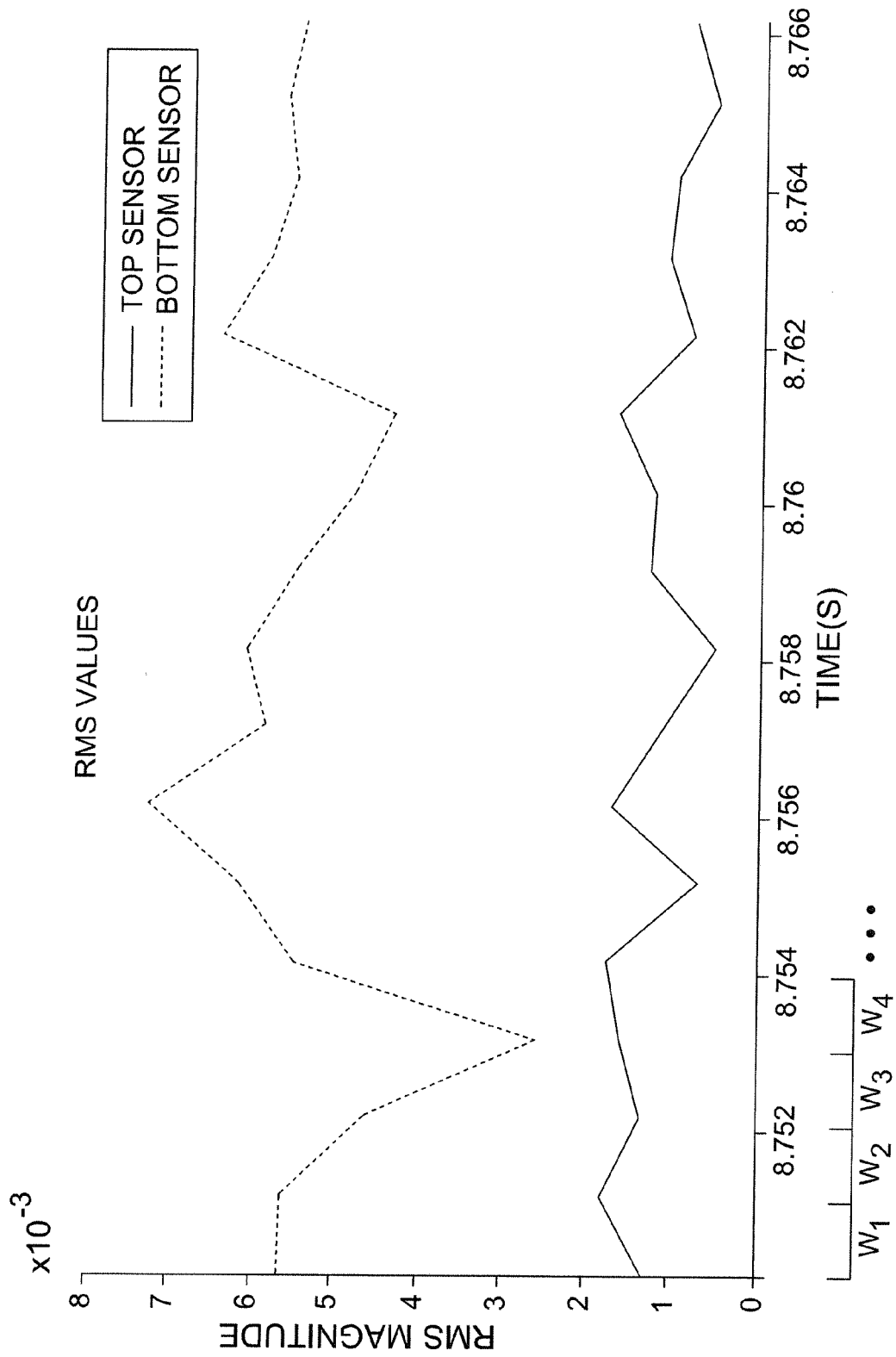
FIGS. 2C and 2D show the RMS magnitudes of the acoustic signals of FIGS. 2A and 2B, respectively.
Figure 2D:
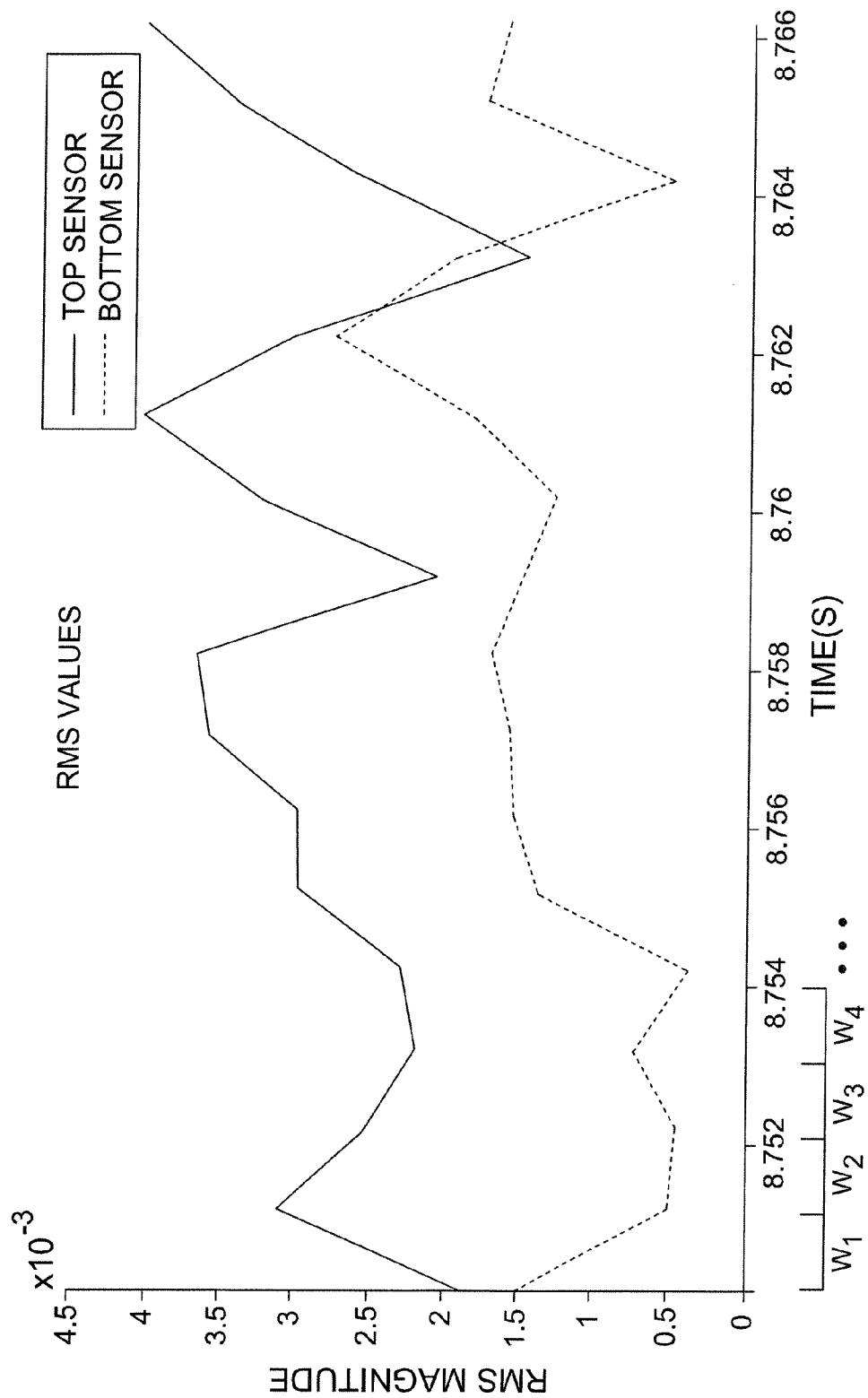

When performing the method of FIG. 5, the processor 104 begins at block 502 and determines whether any more window pairs $w_{k\_pair}$ of the acoustic signals 200 remain to be analyzed. If yes, the processor 104 proceeds to block 504 to begin the analysis on one of the remaining window pairs $w_{k\_pair}$. At block 504 the processor determines the RMS amplitude of each of the windows of the pair $w_{k\_pair}$. FIGS. 2C and 2D show the RMS amplitudes of the acoustic signals 200 shown in FIGS. 2A and 2B, respectively. For each of the windows $w_k$, the processor 104 determines the RMS amplitude over the duration of that window $w_k$.

Once the processor 104 has determined the RMS amplitude of each of the windows of the window pair $w_{k\_pair}$ at block 504, the processor 104 proceeds to block 506 where it determines a power ratio for the window pair $w_{k\_pair}$. The processor 104 determines the power ratio from the RMS amplitude of the shallower sensor 124a (RMS$_{shallow}$) and the RMS amplitude of the deeper sensor 124b (RMS$_{deep}$). For the shallower sensor 124a, the power ratio (PR$_{shallow}$) is $$PR_{shallow} = (RMS^2_{shallow})/(RMS^2_{shallow} + RMS^2_{deep}). \quad (1)$$

For the deeper sensor 124b, the power ratio (PR$_{deep}$) is $$PR_{deep} = (RMS^2_{deep})/(RMS^2_{shallow} + RMS^2_{deep}). \quad (2)$$

As the depicted embodiment of the system includes only the two sensors 124, PR$_{deep}$ also equals $(1-PR_{shallow})$. In an alternative embodiment (not depicted), other metrics aside from power may be used as a proxy for loudness. For example, magnitude may be used instead of power, and instead of a power ratio the processor 104 may determine a magnitude ratio in which MR$_{shallow}$=RMS$_{shallow}$/(RMS$_{shallow}$+RMS$_{deep}$), and in which the processor 104 may analogously determine MR$_{deep}$. Both the power and magnitude ratios described above are exemplary types of loudness ratios, and in alternative embodiments other types of loudness ratios or variations on the foregoing power and magnitude ratios are possible. For example, in another alternative embodiment (not depicted), the processor 104 may use a value other than RMS amplitude when determining power or magnitude ratios, such as peak or average non-RMS amplitude, at block 504.

After determining the power ratios, the processor 104 proceeds to block 508. At block 508 the processor 104 obtains an indication of the relative depth of the acoustic event by comparing the power ratios to a ratio threshold. If PR$_{shallow}$ exceeds the ratio threshold, the processor 104 determines that the window pair $w_{k\_pair}$ from which PR$_{shallow}$ was determined indicates that the acoustic event is louder at the shallower sensor 124a than the deeper sensor 124b, which indicates the acoustic event is above the shallower sensor 124a. Analogously, if PR$_{deep}$ exceeds the ratio threshold, the processor 104 determines that the window pair $w_{k\_pair}$ from which PR$_{deep}$ was determined indicates that the acoustic event is louder at the deeper sensor 124b than the shallower sensor 124a, which indicates the acoustic event is louder at and below the deeper sensor 124b. In the depicted embodiment, the ratio threshold is set to approximately 0.75. In alternative embodiments (not depicted), the ratio threshold may be set anywhere from 0 to 1 or at any value within that range, and PR$_{shallow}$ and PR$_{deep}$ may be compared to different ratio thresholds.

Setting the ratio threshold above 0.50 is beneficial in that the higher the ratio threshold, the more powerful the acoustic signal 200 from one of the sensors 124 is before the processor 104 concludes that the window pair $w_{k\_pair}$ indicates the relative location of the acoustic event. For example, if the window pair $w_{k\_pair}$ has captured only white noise and at a given instant RMS shallow and RMS$_{deep}$ are approximately equal to each other, PR$_{shallow}\approx$PR$_{deep}\approx$0.5.

By setting the ratio threshold substantially above 0.5, such as at 0.75, the processor 104 will exclude from consideration those window pairs $w_{k\_pair}$ that contain insufficient information to be considered useful.

Once the processor 104 has finished analyzing all the window pairs $w_{k\_pair}$ for the acoustic signals according to blocks 502 to 508, the processor proceeds from block 502 to 510 and determines how many of the window pairs $w_{k\_pair}$ indicate the acoustic event is above the shallower sensor 124a (i.e.: $PR_{shallow} \geq$ the ratio threshold) and how many of the window pairs $w_{k\_pair}$ indicate the acoustic event is below the deeper sensor 124b (i.e. $PR_{deep} \geq$ the ratio threshold). In the depicted embodiment, the processor 104 determines that the acoustic event is above the shallower sensor 124a if ($PR_{shallow} \geq$ the ratio threshold) for more of the window pairs $w_{k\_pair}$ than ($PR_{deep} \geq$ the ratio threshold), and analogously determines that the acoustic event is below the deeper sensors 124b if ($PR_{deep} \geq$ the ratio threshold) for more of the window pairs $w_{k\_pair}$ than ($PR_{shallow} \geq$ the ratio threshold). In an alternative embodiment, the processor 104 may determine the relative depth of the acoustic event differently. For example, the processor 104 may determine the average values of $PR_{deep}$ and $PR_{shallow}$ for all the window pairs $w_{k\_pair}$, and determine the relative depth of the acoustic event as being above the shallower sensor 124a if $PR_{shallow}$ has the higher average value and below the deeper sensor 124b if $PR_{deep}$ has the higher average value.

Figure 3:
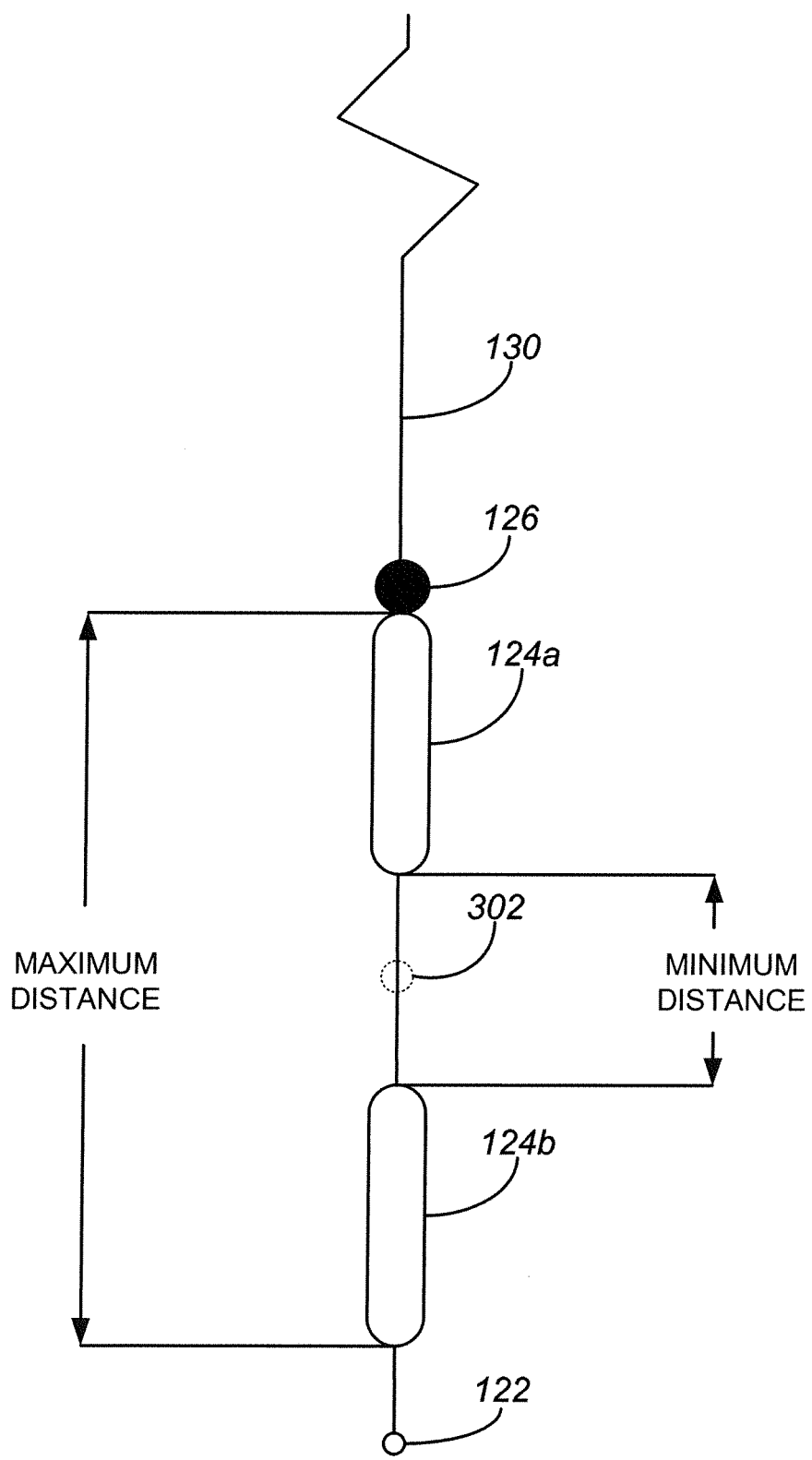
FIG. 3 shows two sensors in the form of pressure sensing regions that form part of a fiber optic sensor assembly used in the system of FIG. 1A.

FIG. 3 shows a detailed view of the bottom of the fiber optic sensor assembly. As the sensors 124 are distributed, the acoustic signals 200 may be generated as a result of the acoustic event being detected anywhere along the length of the sensors 124. Consequently, the minimum time that passes between the acoustic event being detected in the two acoustic signals 200 corresponds to the time it takes for sound to travel from the bottom end of the shallower sensor 124a to the top end of the deeper sensor 124b. This distance is labelled "minimum distance" in FIG. 3, and the time it takes for sound waves generated by the acoustic event to travel the minimum distance is the (minimum distance)/(speed of sound in the wellbore 134). In an exemplary embodiment, the minimum distance is 0.108 m, the wellbore 134 is filled with a fluid that is mainly water and in which sound travels 1484 m/s, and the minimum time lag is accordingly 0.0000728 s. Similarly, the time it takes for sound to travel from the top end of the shallower sensor 124a to the bottom end of the deeper sensor 124b is the "maximum distance" and is labelled in FIG. 3. The time it takes for the acoustic event to travel the maximum distance is the (maximum distance)/(speed of sound in the wellbore 134). In the exemplary embodiment, the maximum distance is 0.75 m, and the maximum time lag is accordingly 0.0005054 s.

In the depicted embodiment, given the relatively small distance between the sensors 124 relative to the depth of the wellbore 134, the processor 104 does not attempt to determine whether the time difference between when the acoustic signals arrive at the sensors 124 is between the minimum and maximum time lags. Instead, the processor 104 uses all acoustic signals when determining the relative depth of the acoustic event regardless of when they are generated. In so doing, the processor 104 accepts a higher margin of error in exchange for implementing a simpler algorithm.

In an alternative embodiment (not depicted), if the processor 104 determines that sound waves generated simultaneously by the same acoustic event arrives at the sensors 124 at times differing by less than the minimum time lag, the processor 104 does not use the portion of the acoustic signals 200 corresponding to that acoustic event. In another alternative embodiment (not depicted), the processor 104 may use those signals 200 to determine whether the acoustic event is located, for example, between the sensors 124. Analogously, if the processor 104 determines that sound generated simultaneously from the same acoustic event arrives at the sensors 124 at times differing by more than the minimum time lag, the processor 104 does not use the portion of the acoustic signals 200 corresponding to that acoustic event, as they may be indicative of one or both of the sensors 124 measuring an acoustic reflection or of some type of measurement artefact. Instead, the processor 104 either actuates the spooling device 130 and moves to a new pair of depths to obtain new acoustic signals 200, or uses portions of the acoustic signals 200 in which the acoustic event as recorded by the two sensors 124 is separated by a time between the minimum and maximum time lags.

In FIG. 3, the minimum and maximum distances are determined relative to the tops and bottoms of the sensors 124. However, in alternative embodiments (not depicted), these distances may be determined relative to different points on the sensors 124. For example, it may be assumed for convenience that any measurements obtained using the sensors 124 are obtained at their midpoints, thus making the maximum and minimum distances equal to each other. Alternatively, instead of distributed sensing regions, non-distributed point sensors may be used, which also results in the minimum and maximum distances being equal to each other.

If, because of the time it takes for sound to travel from one of the sensors 124a to the other of the sensors 124b and because of the duration selected for the windows, window pairs $w_{k\_pair}$ do not contain corresponding portions of the acoustic event, the processor 104 may time stagger the acoustic signals 200 relative to the windows so that each of the windows in a window pair $w_{k\_pair}$ contain corresponding portions of the acoustic event to compare to each other.

In the depicted embodiment, the processor 104 determines a deemed reference depth 302 and for simplicity expresses the depth of the acoustic event relative to the deemed reference depth. The deemed reference depth 302 in the depicted embodiment is the midpoint between the sensors 124. If the processor 104 determines that the acoustic event is above the shallower sensor 124a, then the processor 104 tells a user of the system 100 that the acoustic event is above the deemed reference depth 302. Conversely, if the processor 104 determines that the acoustic event is below the deeper sensor 124b, then it tells the user that the acoustic event is below the deemed reference depth 302. Doing so allows information to be presented to the user in an easier to user format than if the processor 104 uses the depths of the shallower and deeper sensors 124 as reference depths. While in the depicted embodiment the reference depth 302 is at the midpoint of the sensors 124, in alternative embodiments (not depicted) the reference depth 302 may be located elsewhere, such as along one of the sensors 124, above the shallower sensor 124a, or below the deeper sensor 124b.

Figure 7:
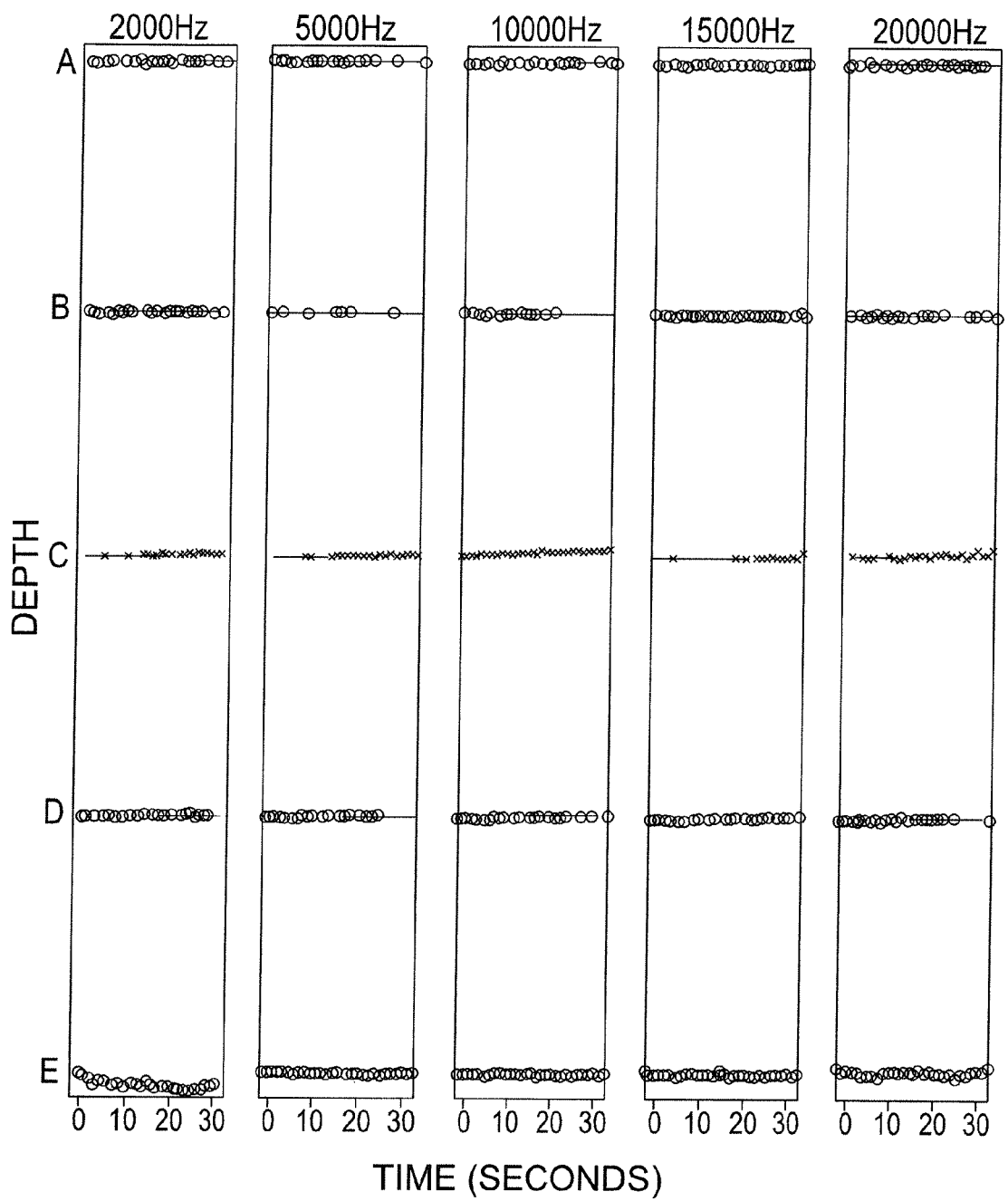
FIG. 7 shows plots indicating whether the acoustic event is shallower or deeper than a deemed reference depth of the system of FIG. 1A at various deemed reference depths.

Referring now to FIG. 7, in one embodiment the processor 104 may graph, using at least two types of indicators such as the Xs and Os shown on the plots in FIG. 7, whether the acoustic event is above or below the reference depth 302 at various reference depths and over various times over which the acoustic event is measured. In FIG. 7, plots are shown in which the acoustic signals 200 are filtered using bandpass filters of 2,000 Hz, 5,000 Hz, 10,000 Hz, 15,000 Hz, and 20,000 Hz prior to being analyzed by the processor 104, and according to five known reference depths 302 A-E in the wellbore 134. Xs are used to indicate when one of the window pairs $w_{k\_pair}$ indicates that the acoustic event is above the reference depth 302 ($PR_{shallow} \geq$ the ratio threshold), while Os are used to indicate when one of the window pairs $w_{k\_pair}$ indicates that the acoustic event is below the reference depth 302 ($PR_{deep} \geq$ the ratio threshold). A blank in the plots along the horizontal axis indicates that either no measurement was taken at that time or that neither $PR_{shallow}$ nor $PR_{deep}$ exceeded their respective ratio thresholds.

Examining, for example, the 10,000 Hz plot at depths A and B, the processor 104 determines that for each of the window pairs $w_{k\_pair}$ in which either $PR_{deep}$ or $PR_{shallow} \geq$ the ratio threshold the window pair $w_{k\_pair}$ indicates that the acoustic event is below the deeper sensor 124b. In accordance with the methods described above, the processor 104 accordingly determines that the acoustic event is below reference depths 302 A and B. At depth C, the processor 104 analogously determines that for each of the window pairs $w_{k\_pair}$ in which either $PR_{deep}$ or $PR_{shallow} \geq$ the ratio threshold, the window pair $w_{k\_pair}$ indicates that the acoustic event is above the shallower sensor 124a. The processor 104 accordingly determines that the acoustic event is above depth C. Reviewing this plot accordingly allows the user of the system 100 to determine that the acoustic event is located between depths B and C. As the sensors 124 are lowered deeper into the wellbore 134, the processor 104 at depths D and E determines that another acoustic event, different from the one detected between depths B and C, is below each of these reference depths 302.

Figure 8A:
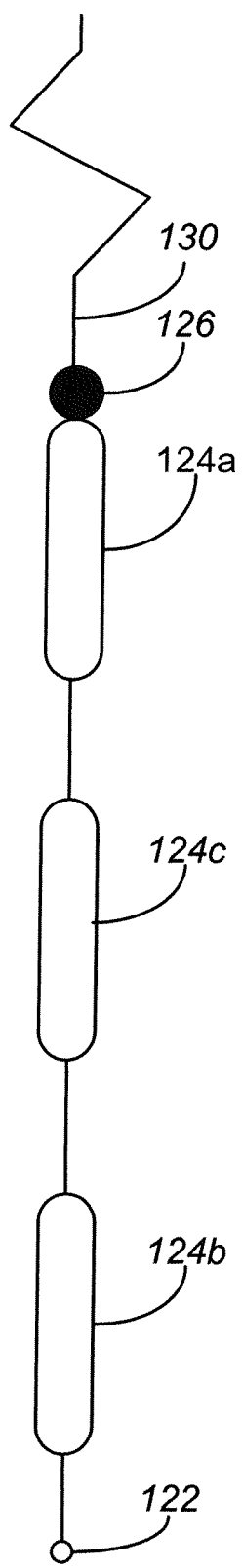
FIGS. 8A and 8B show two additional embodiments of the fiber optic sensor assembly that can be used in the system of FIG. 1A.

Some acoustic events of relatively low frequencies may resist attenuation particularly well within the wellbore 134, and an alternative embodiment of the fiber optic assembly, such as that shown in FIG. 8, may be used accordingly. In FIG. 8, a middle sensor 124c is positioned between the top and bottom sensors 124a,b, and is used to obtain a third acoustic signal (not depicted) at a third different and known depth within the wellbore 134. The relative depth of the acoustic event can then be determined relative to the middle sensor 124c and one or both of the shallower sensor 124a and the deeper sensor 124b, which can be used in addition to the relative depth determined relative to the shallower and deeper sensors 124a,b. Because higher frequencies attenuate more quickly within the wellbore 134 than lower frequencies, the shallower and deeper sensors 124a,b can be used to measure acoustic events having lower frequencies than measured by the middle sensor 124c and one of the top and bottom sensor 124a,b. In one embodiment, while the middle sensor 124c and one of the top and bottom sensors 124a,b is used to determine the relative depth of the acoustic event according to the one of the methods described above, the top and bottom sensors 124a,b can be used to determine the relative depth of the acoustic event in accordance with either an identical method or an alternative method, such as one of those described in PCT patent application having serial number PCT/CA2011/000031, publication number WO/2011/091505, and entitled "Method for Detecting and Locating Fluid Ingress in a Wellbore". The midpoints of the shallower and deeper sensors 124a,b may be, for example, approximately 5 m apart, while the midpoint of the middle sensor 124c may be located 2.5 m from each of the shallower and deeper sensors 124a,b.

Figure 8B:
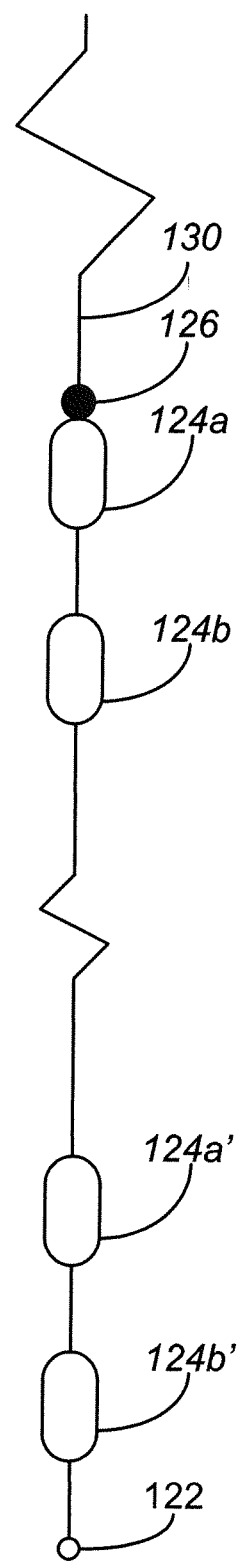

Referring now to FIG. 8B, there is shown another embodiment of the fiber optic assembly in which there are two pairs of shallower and deeper sensors, the first pair 124a,b and a second pair 124a',b', separated by a certain length of the fiber optic cable 130. This embodiment of the fiber optic assembly may be used, for example, in order to survey the wellbore 134 twice as fast by surveying two halves of the wellbore 134 simultaneously as opposed to using only one pair of the sensors 124 to survey the entire wellbore 134.

Also beneficially, dividing the acoustic signals into the windows $w_1 \ldots w_n$ helps to compensate for non-idealities encountered in the field. Such non-idealities include, for example, multiple acoustic events having sources located at different depths simultaneously making noise, acoustic events having frequencies that vary over time, acoustic reflections, and interference. If, in an ideal situation a first acoustic signal would have a larger RMS amplitude than a second acoustic signal, the non-idealities can result in variance of signal amplitudes and distort the processor 104's analysis. Dividing the acoustic signals into the windows $w_1 \ldots w_n$ helps to mitigate the detrimental effects of such non-idealities better than if a single magnitude ratio were determined using the entirety of the acoustic signals. For example, FIG. 6 shows a pair of acoustic signals 200 in which Channel 1, which corresponds to the acoustic signal measured using the shallower sensor 124a, has a larger RMS magnitude than Channel 2, which corresponds to the acoustic signal measured using the deeper sensor 124b, but in which this is obscured by noise for slightly under half the duration of the signals. With windowing, if the processor 104 is configured to determine that when, for example, at least 45% of the window pairs $w_{k\_pair}$ show that when the magnitude ratio for Channel 1 exceeds the magnitude threshold, the processor 104 is able to correctly determine the relative location from the Channel 1 and 2 signals notwithstanding the presence of noise, which may have prevented the processor 104 from arriving at this determination if only a single magnitude ratio were determined using the entirety of the noise-corrupted signals. The use of windowing allows the portions of the signals relatively unaffected by noise to form the basis of the processor 104's determination.

The processor 104 performs the method of FIG. 5 to determine the power ratio for the window pair $w_{k\_pair}$ in the time domain. In an alternative embodiment and as depicted in FIG. 9, the processor 104 may also determine the power ratio for the window pair $w_{k\_pair}$ in the frequency domain.

Figure 9:
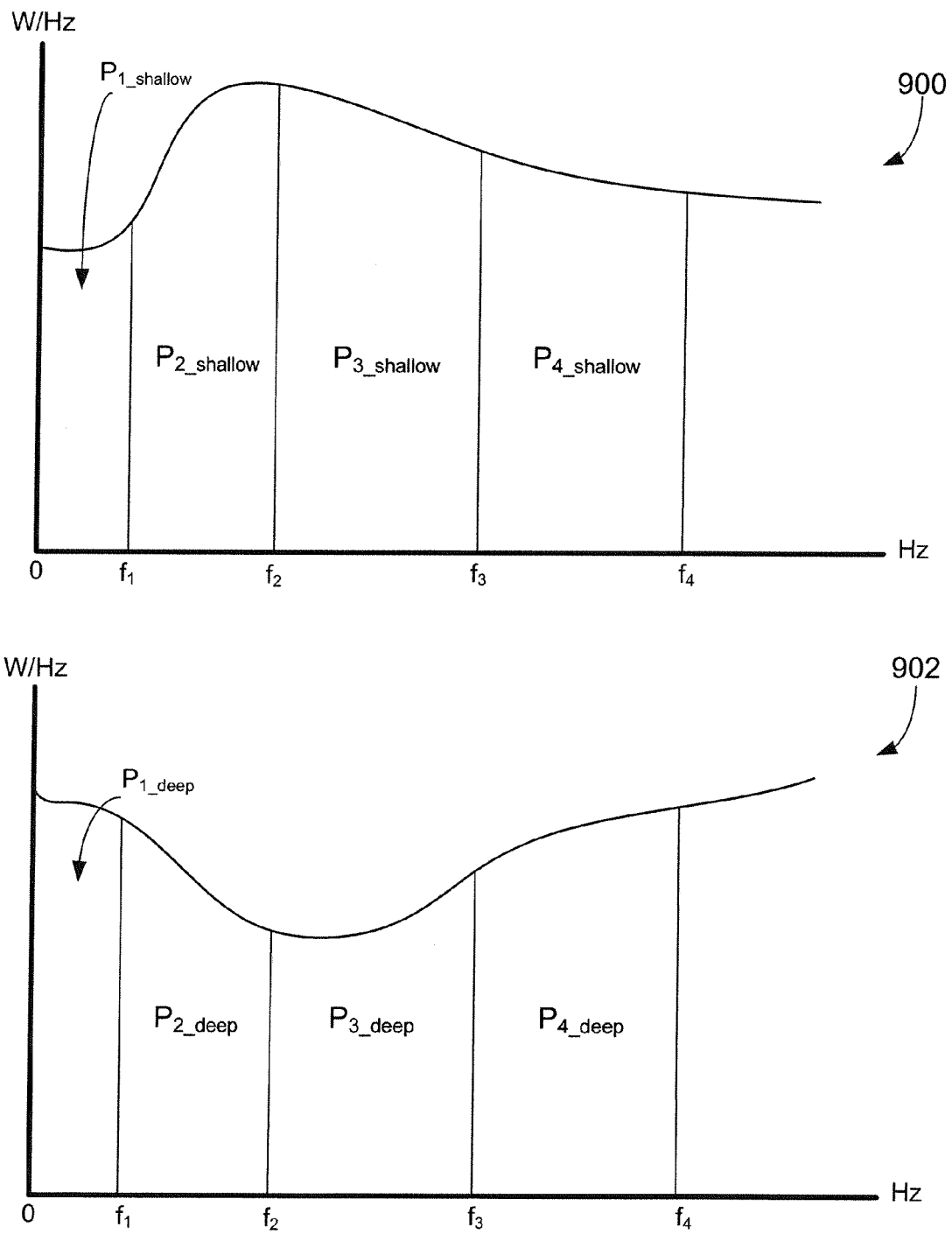
FIG. 9 shows graphs of power spectral density vs. frequency for another pair of acoustic signals acquired using the system of FIG. 1A.

FIG. 9 shows two graphs of power spectral density ("PSD") in W/Hz against frequency in Hz. A top graph 900 shows the PSD obtained by performing a discrete Fourier Transform, such as a Fast Fourier Transform, on one window $w_k$ of the acoustic signal 200a generated by the shallower sensor 124a while a bottom graph 902 shows the PSD obtained by performing the discrete Fourier Transform on one window $w_k$ of the other acoustic signal 200b, which is generated by the deeper sensor 124b, with the windows $w_k$ collectively forming one window pair $w_{k\_pair}$. Five frequencies are marked on each of the graphs 900,902: 0 Hz, $f_1$, $f_2$, $f_3$, and $f_4$. For the top graph 900, the power determined by integrating from 0 Hz to $f_1$ Hz is $P_{1\_shallow}$; the power determined by integrating from $f_1$ to $f_2$ is $P_{2\_shallow}$; the power determined by integrating from $f_2$ to $f_3$ is $P_{3\_shallow}$; and the power determined by integrating from $f_3$ to $f_4$ is $P_{4\_shallow}$. Similarly, for the bottom graph 902, the power determined by integrating from 0 Hz to $f_1$ Hz is $P_{1\_deep}$; the power determined by integrating from $f_1$ to $f_2$ is $P_{2\_deep}$; the power determined by integrating from $f_2$ to $f_3$ is $P_{3\_deep}$; and the power determined by integrating from $f_3$ to $f_4$ is $P_{4\_deep}$.

Accordingly, for any given window pair $w_{k\_pair}$ the power ratio for the shallower sensor 124a, $PR_{j\_k\_shallow}$, where $j \in [1 \ldots 5]$ is $$PR_{j\_k\_shallow} = (P_{j\_k\_shallow})/(P_{j\_k\_shallow} + P_{j\_k\_deep}) \quad (3)$$

while for the deeper sensor 124, $PR_{j\_k\_deep}$ where $j \in [1 \ldots 5]$ is $$PR_{j\_k\_deep} = (P_{j\_k\_deep})/(P_{j\_k\_shallow} + P_{j\_k\_deep}). \quad (4)$$

As in the time domain analysis of FIG. 5, for any frequency range corresponding to $j \in [1 \ldots 5]$ the processor 104 can determine whether one or both of the power ratios exceed their respective ratio thresholds, and then determine whether the acoustic event occurred above the shallower sensor 124a or below the deeper sensor 124b by determining how many of the window pairs $w_{k\_pair}$ indicate the acoustic event is above the shallower sensor 124a (i.e.: $PR_{j\_k\_shallow} \geq$ the ratio threshold) and how many of the window pairs $w_{k\_pair}$ indicate the acoustic event is below the deeper sensor 124b (i.e. $PR_{j\_k\_deep} \geq$ the ratio threshold).

As discussed above, in the time domain analysis of FIG. 5 the processor 104 filters the acoustic signals 200 prior to windowing and determining the relative depth of the acoustic event. When performing the frequency domain analysis the processor 104 can forego filtering and window the unfiltered acoustic signals 200. The processor 104 generates the graphs 900,902 for all frequencies and then considers frequencies or frequency ranges of interest. For example, based on the graphs 900,902 the processor is able to determine that for the window pair $w_{k\_pair}$ whose PSD is shown, the acoustic signal 200a that the shallower sensor 124a generates has more power between $f_1$ and $f_3$ than the acoustic signal 200b that the deeper sensor 124b generates between $f_1$ and $f_3$. The Fourier Transform allows the processor 104 to identify acoustic events at specific frequencies or frequency ranges without the filtering that would be performed when using the time domain analysis of FIG. 5.

While in FIG. 9 n=5, in alternative embodiments (not depicted) n may be any suitable number less than or greater than 5. Any $f_j$ and $f_{j+1}$ where $j \in [1 \ldots n]$, $i \in [1 \ldots n-1]$ may be selected so that the processor 104 may isolate and search specifically for acoustic events that occur within $f_j$ and $f_{j+1}$. Doing this allows the processor 104 to search specifically for acoustic events occurring in certain frequency ranges.

In the foregoing embodiments obtaining and dividing the acoustic signals 200 into windows is performed by having the data acquisition box 110 output the acoustic signals 200 to the processor 104, and then having the processor 104 divide the acoustic signals 200 into the windows. In alternative embodiments (not depicted), obtaining and dividing the acoustic signals 200 may be performed by having the data acquisition box 110 output the windows to the processor 104, and having the processor 104 analyze the windows without dividing the acoustic signals 200 itself. Once the processor 104 receives a sufficient number of window pairs $w_{k\_pair}$, the processor 104 will have obtained the acoustic signals 200 and is able to determine the relative location of the acoustic event without having divided the acoustic signals 200 into windows itself.

The processor 104 used in the foregoing embodiments may be, for example, a microprocessor, microcontroller, programmable logic controller, field programmable gate array, or an application-specific integrated circuit. Examples of the computer readable medium 106 are non-transitory and include disc-based media such as CD-ROMs and DVDs, magnetic media such as hard drives and other forms of magnetic disk storage, semiconductor based media such as flash media, random access memory, and read only memory.

It is contemplated that any part of any aspect or embodiment discussed in this specification can be implemented or combined with any part of any other aspect or embodiment discussed in this specification.

For the sake of convenience, the exemplary embodiments above are described as various interconnected functional blocks. This is not necessary, however, and there may be cases where these functional blocks are equivalently aggregated into a single logic device, program or operation with unclear boundaries. In any event, the functional blocks can be implemented by themselves, or in combination with other pieces of hardware or software.

While particular embodiments have been described in the foregoing, it is to be understood that other embodiments are possible and are intended to be included herein. It will be clear to any person skilled in the art that modifications of and adjustments to the foregoing embodiments, not shown, are possible.

The invention claimed is:

1. A method for determining relative location of an acoustic event within a channel, the method comprising:
   (a) obtaining two acoustic signals at two different and known locations in the channel, wherein at least one of the acoustic signals includes the acoustic event;
   (b) dividing each of the acoustic signals into windows, each of which has a certain duration;
   (c) determining relative loudnesses of pairs of the windows, wherein each of the pairs comprises one window from one of the acoustic signals and another window from the other of the acoustic signals that substantially overlap each other in time; and
   (d) determining a relative location of the acoustic event relative to the two known locations from the relative loudnesses.

2. The method of claim 1 wherein the channel comprises a pipeline and the acoustic event comprises a leak in the pipeline.

3. The method of claim 2 wherein both of the acoustic signals include the acoustic event.

4. The method of claim 3 wherein the windows that comprise any one of the pairs of the windows are time staggered such that the acoustic event is represented in both the windows of the pair.

5. The method of claim 2 wherein obtaining the two acoustic signals comprises simultaneously measuring the acoustic event at the two different and known locations along the pipeline.

6. The method of claim 2 wherein the windows that comprise any one of the pairs of the windows represent concurrent portions of the acoustic signals.

7. The method of claim 2 wherein the windows into which any one of the acoustic signals is divided do not overlap with each other.

8. The method claim 2 wherein determining the relative loudnesses of each of the pairs of the windows comprises determining relative powers of each of the pairs of windows according to a method comprising:
   (a) for each of the windows of the pair, determining the RMS amplitude of the portion of the acoustic signal within the window; and
   (b) determining a loudness ratio comprising the ratio of the square of the RMS amplitude of a first of the windows of the pair relative to the sum of the squares of the RMS amplitudes of both of the windows of the pair.

9. The method of claim 2 wherein determining the relative loudnesses of each of the pairs of the windows comprises determining relative magnitudes of each of the pairs of windows according to a method comprising:
  (a) for each of the windows of the pair, determining the RMS amplitude of the portion of the acoustic signal within the window; and
  (b) determining a loudness ratio comprising the ratio of the RMS amplitude of a first of the windows of the pair relative to the total RMS amplitudes of both of the windows of the pair.

10. The method of claim 1 wherein the channel comprises an observation well and the acoustic event comprises creation or expansion of fractures in a fracking well.

11. The method of claim 1 wherein:
  (a) the channel comprises a wellbore;
  (b) the relative location is relative depth; and
  (c) the acoustic event comprises fluid flowing from formation into the wellbore, fluid flowing from the wellbore into the formation, or fluid flowing across any casing or tubing located within the wellbore.

12. The method claim 11 wherein determining the relative loudnesses of each of the pairs of the windows comprises determining relative powers of each of the pairs of windows according to a method comprising:
  (a) for each of the windows of the pair, determining the RMS amplitude of the portion of the acoustic signal within the window; and
  (b) determining a loudness ratio comprising the ratio of the square of the RMS amplitude of a first of the windows of the pair relative to the sum of the squares of the RMS amplitudes of both of the windows of the pairs.

13. The method of claim 12 wherein determining the relative depth of the acoustic event comprises:
  (a) obtaining an indication of the relative depth of the acoustic event from the loudness ratio; and
  (b) determining whether the acoustic event is above the shallower of the two known depths or below the deeper of the two known depths by comparing each of the loudness ratios of the pairs of the windows to a ratio threshold, wherein one of the pairs indicates the acoustic event is above the shallower of the two known depths when the loudness ratio indicates that the acoustic event is louder at the shallower of the two known depths than the deeper of the two known depths, and one of the pairs indicates the acoustic event is below the deeper of the two known depths when the loudness ratio indicates that the acoustic event is louder at the deeper of the two known depths than the shallower of the two known depths.

14. The method of claim 13 wherein determining whether the acoustic event is above the shallower of the two known depths or below the deeper of the two known depths comprises:
  (a) determining how many of the pairs indicates that the acoustic event is above the shallower one of the two known depths or below the deeper one of the two known depths; and
  (b) determining whether the acoustic event is above the shallower one of the two known depths or below the deeper one of the two known depths from how many of the pairs indicate that the acoustic event is above the shallower one of the two known depths or below the deeper one of the two known depths.

15. The method of claim 14 wherein the acoustic event is determined to be above the shallower one of the two known depths when at least half of the pairs indicate that the acoustic event is above the shallower one of the two known depths, and otherwise is determined to be below the deeper of the two known depths.

16. The method of claim 13 further comprising determining that the acoustic event is above a deemed reference depth when the acoustic event is determined to be above the shallower one of the two known depths, and determining that the acoustic event is below the deemed reference depth when the acoustic event is determined to be below the shallower of the two known depths.

17. The method of claim 16 where the deemed reference depth is midway between the two known depths.

18. The method of claim 16 further comprising:
  (a) determining a measured time difference of the acoustic event as recorded in the acoustic signals;
  (b) comparing the measured time difference to a minimum time difference;
  (c) only using the loudness ratio to determine the relative depth of the acoustic event if the measured time difference equals or exceeds the minimum time difference;
  (d) obtaining new acoustic signals corresponding to new known depths if the measured time difference is less than the minimum time difference, wherein the measured time difference of the acoustic event as recorded in the new acoustic signals equals or exceeds the minimum time difference; and
  (e) determining the relative depth of the acoustic event using the new acoustic signals.

19. The method of claim 18 wherein obtaining the acoustic signals comprises measuring the acoustic event at the two different and known depths using a fiber optic sensor assembly comprising a fiber optic cable having two pressure sensing regions spaced from each other, and wherein each of the pressure sensing regions has top and bottom ends and the minimum time difference is the time for sound to travel between the top end of the deeper one of the pressure sensing regions to the bottom end of the shallower one of the pressure sensing regions.

20. The method of claim 16 further comprising:
  (a) determining a measured time difference of the acoustic event as recorded in the acoustic signals;
  (b) comparing the time difference to a maximum time difference;
  (c) only using the magnitude ratio to determine the relative depth of the acoustic event if the time difference is less than or equals the maximum time difference;
  (d) obtaining new acoustic signals corresponding to new known depths if the measured time difference exceeds the minimum time difference, wherein the measured time difference of the acoustic event as recorded in the new acoustic signals is less than or equal to the maximum time difference; and
  (e) determining the relative depth of the acoustic event using the new acoustic signals.

21. The method of claim 20 wherein obtaining the acoustic signals comprises measuring the acoustic event at the two different and known depths using a fiber optic sensor assembly comprising a fiber optic cable having two pressure sensing regions spaced from each other, and wherein each of the pressure sensing regions has top and bottom ends and the maximum time difference is the time for sound to travel between the bottom end of the deeper one of the pressure sensing regions to the top end of the shallower one of the pressure sensing regions.

22. The method of claim 13 further comprising graphing, using at least two types of indicators, on a plot comprising depth whether the acoustic event is above the shallower of the two known depths or below the deeper of the two known depths at various depths over which the acoustic event is measured.

23. The method of claim 22 wherein the indicators comprise two different colors.

24. The method of claim 22 wherein the plot further comprises time plotted versus the depth, and wherein the plot shows whether the acoustic event is above the shallower of the two known depths or below the deeper of the two known depths at various depths and times over which the acoustic event is measured.

25. The method of claim 11 further comprising
(a) obtaining a third acoustic signal at a third different and known depth in the wellbore, wherein the third acoustic signal includes the acoustic event;
(b) determining the relative depth of the acoustic event relative to one or both of:
  (i) one of the two different and known depths and the third different and known depth; and
  (ii) the other of the two different and known depths and the third different and known depth.

26. The method of claim 25 wherein the relative depth of the acoustic event is determined relative to the two different and known depths when the acoustic event is less than about 2 kHz, and the relative depth of the acoustic event is determined relative to the third different and known depth and one of the other different known depths when the acoustic event is greater than about 2 kHz.

27. The method of claim 1 wherein determining relative loudnesses of pairs of the windows comprises comparing power of one of the acoustic signals between two frequencies to power of the other of the acoustic signals between the two frequencies.

28. A non-transitory computer readable medium having encoded thereon statements and instructions to cause a processor to perform a method for determining relative location of an acoustic event within a channel, the method comprising:
(a) obtaining two acoustic signals at two different and known locations in the channel, wherein at least one of the acoustic signals includes the acoustic event;
(b) dividing each of the acoustic signals into windows, each of which has a certain duration;
(c) determining relative loudnesses of pairs of the windows, wherein each of the pairs comprises one window from one of the acoustic signals and another window from the other of the acoustic signals that substantially overlap each other in time; and
(d) determining a relative location of the acoustic event relative to the two known locations from the relative loudnesses.

* * * * *